United States Patent
Kilic et al.

(12)

(10) Patent No.: US 8,394,624 B2
(45) Date of Patent: Mar. 12, 2013

(54) PROCESS FOR PRESERVING BIOLOGICAL MATERIALS FOR EXTENDED PERIODS OF TIME

(75) Inventors: Ali O. Kilic, Bear (DE); John S. Novak, Fresh Meadows, NY (US); Karen Vaughn, Houston, TX (US); Pierre Meyers, Buc (FR)

(73) Assignees: American Air Liquide, Inc., Fremont, CA (US); Air Liquide Healthcare American Corporation, Houston, TX (US)

( * ) Notice: Subject to any disclaimer, the term of this patent is extended or adjusted under 35 U.S.C. 154(b) by 315 days.

(21) Appl. No.: 12/695,437

(22) Filed: Jan. 28, 2010

(65) Prior Publication Data

US 2010/0196996 A1  Aug. 5, 2010

Related U.S. Application Data

(60) Provisional application No. 61/148,608, filed on Jan. 30, 2009, provisional application No. 61/161,508, filed on Mar. 19, 2009.

(51) Int. Cl.
*C12N 1/04* (2006.01)
*C12N 1/00* (2006.01)
*C12S 3/00* (2006.01)
*B01J 19/14* (2006.01)

(52) U.S. Cl. ............ 435/260; 435/243; 534/7; 34/282; 34/410; 422/1; 422/40

(58) Field of Classification Search .................... None
See application file for complete search history.

(56) References Cited

U.S. PATENT DOCUMENTS

| | | | |
|---|---|---|---|
| 3,677,024 A | 7/1972 | Segall | |
| 3,682,776 A | 8/1972 | Grundmann et al. | |
| 3,772,153 A | 11/1973 | De Roissart | |
| 4,423,600 A | 1/1984 | McKenna | |
| 5,328,821 A | 7/1994 | Fisher et al. | |
| 5,362,622 A | 11/1994 | O'Dell et al. | |
| 5,462,861 A * | 10/1995 | Spencer et al. | 435/41 |
| 5,719,174 A | 2/1998 | Sainsbury et al. | |
| 6,204,375 B1 | 3/2001 | Lader | |
| 6,521,275 B1 | 2/2003 | Mercogliano et al. | |
| 6,528,641 B2 | 3/2003 | Lader | |
| 6,777,210 B1 | 8/2004 | Pasloske et al. | |
| 7,056,673 B2 | 6/2006 | Kamme et al. | |
| 7,138,226 B2 | 11/2006 | Vincek et al. | |

FOREIGN PATENT DOCUMENTS

| | | |
|---|---|---|
| FR | 1339669 | 10/1963 |
| JP | 59082301 | 5/1984 |

OTHER PUBLICATIONS

Tachibana, M et al "Expression of Androgen Receptor in Mouse Eye Tissues", Invest Ophthalmol Vis Sci, 2000, 41(1), pp. 64-66.*
SuperBioChips Laboratories "Tissue Array" <URL:http://www.tissue-array.com/ver3/index.php>, 2005, archived online May 20, 2007, 1 page.*
University of Bristol, "Histological Fixatives", School of Veterinary PathologyXP002617139, Jul. 20, 2005; Retrieved from URL:http://www.bristol.ac.uk/vetpath/cpl/histfix.htm [retrieved Feb. 18, 2011], 5 pages.
Database WPI, Week 198738, Thomson Scientific, London, GB; AN 1987-270009, XP002617138, & SU 1 289 437 A. (Kaza Clinical Surge) Feb. 15, 1987, English Abstract, 1 page.
PCT Search Report and Written Opinion for PCT/US2010/022379, 13 pages, Feb. 9, 2011.
Nomenclature Committee of the International Union of Biochemistry and Molecular Biology, "Enzyme Nomenclature" from Enzyme Nomenclature 1992, Academic Press, San Diego, California, ISBN 0-12-227164-5, accessed at http://www.chem.qmul.ac.uk/iubmgb/enzyme/ on May 18, 2012, 6 pages.
Nomenclature Committee of the International Union of Biochemistry and Molecular Biology, digital table of contents for Enzyme Nomenclature 1992, Academic Press, San Diego, California, ISBN 0-12-227164-5, accessed at http://www.chem.qmul.ac.uk/iubmgb/enzyme/EC3/1/ on May 18, 2012, 2 pages.
Nomenclature Committee of the International Union of Biochemistry and Molecular Biology ("IUBMB"), "Oligonucleotidase," Enzyme Nomenclature 1992, section EC 3.1.13,3, Academic Press, San Diego, California, ISBN 0-12-227164-5, accessed at http://www.chem.qmul.ac.uk/iubmgb/enzyme/EC3/1/13/3.html on May 18, 2012, 1 page.

* cited by examiner

*Primary Examiner* — Chris R Tate
*Assistant Examiner* — Aaron J Kosar
(74) *Attorney, Agent, or Firm* — Allen E. White

(57) ABSTRACT

The present invention provides for a process for preserving biological material. The process comprises subjecting the biological material to a fixation process and then packaging the biological material in a container under a controlled atmosphere of noble gas. In the process, the controlled atmosphere of noble gas utilized comprises one or more noble gases selected from argon, xenon, helium, neon, krypton and radon. The process optionally also utilizes one or more additional gases selected from nitric oxide, hydrogen, hydrogen sulfide, carbon monoxide, carbon dioxide, nitrogen and oxygen. This process allows for the long term storage of the biological material.

17 Claims, No Drawings

PROCESS FOR PRESERVING BIOLOGICAL MATERIALS FOR EXTENDED PERIODS OF TIME

CROSS REFERENCE TO RELATED APPLICATION

This application claims the benefit of U.S. Provisional Application Nos. 61/148,608, filed Jan. 30, 2009 and 61/161,508 filed Mar. 19, 2009, the entire contents of which are incorporated herein by reference.

FIELD OF THE INVENTION

The present invention is related to a method for preserving the biochemical and structural integrity of biological materials to be used as immunohistological/histopathological samples in the biological and medical fields, with particular emphasis on use for research purposes and diagnosis and prognosis of specific conditions. More specifically, the present invention is related to a method for decreasing or preventing, over time, the degradation of bio-molecules such as RNA, DNA and proteins in biological materials that are to be stored for later biomedical use and/or research.

BACKGROUND

Due to the ever increasing amount of ongoing research in the biological and medical arenas, there is a vast need for readily available biological materials in which not only the structural integrity, but also the cellular/biological integrity, of the biological materials is preserved so that such materials can be used by biological and medical diagnosticians/researchers for extended periods after the preservation of these materials. Such materials are very important in carrying out research for medical purposes such as cancer research, Alzheimer's research, etc and also as part of the diagnosis of specific diseases as well as following the advancement or prognosis of such diseases. As a result of this need, there is an ongoing increase in the demand for a process that will not only decrease, but also possibly prevent, over time, the degradation of the structural aspects of the biological materials as well as the genetic integrity of such materials. More specifically, in the biological and medical fields, it is desirable to have biological materials (for example, the DNA, RNA and proteins) which have undergone very limited, if any, degradation of the cellular components of the biological materials over a period of time. Such preservation processes would allow further analysis of specific biological materials at a later date or would allow such biological materials to be used at a later date in additional tests or studies.

While in the living host, there are mechanisms which allow for the repair of cellular components such as DNA, RNA and proteins. However, once the tissue is excised or separated from the living host, this repair ceases and the cellular components begin to rapidly break down. A variety of prior art processes are available that allow for the preservation of human and/or animal tissue, including at the individual cellular level. For example, tissue such as biopsies are typically stored as formaldehyde-fixed paraffin-embedded samples (FFPE) thereby allowing for histopathological examination of the preserved sample. FFPE's are prepared by dipping a sample in a formaldehyde solution for a period of time—in recent years using a formaldehyde solution buffered to pH 7.0—followed by embedding the sample in paraffin for storage.

In addition, a variety of methods have been proposed for addressing the issue of nucleic acid preservation from degradation. One of these methods as disclosed in U.S. Pat. No. 6,204,375 involves using specific chemicals and/or chemical reagents such as sulfate salts, while another method as disclosed in U.S. Pat. No. 7,138,226 involves the use of non-aqueous composition of 5-20% polyethylene glycol and 80-95% methanol. Other methods of bio-molecule preservation include inhibition of RNA degrading enzymes such as ribonucleases as disclosed in U.S. Pat. No. 6,777,210 and biological proteases as disclosed in U.S. Pat. No. 3,682,776. Cryo-preservation using ultra low temperatures alone or in combination with chemical solutions has also been demonstrated to be an effective means of preserving bio-molecules in a frozen state as disclosed in Japanese Patent No. 59082301, U.S. Pat. Nos. 4,423,600 and 5,328,821.

The use of inert gases for organ preservation under ultra-hyperbaric pressure and ultra low temperatures has also been described in U.S. Pat. No. 3,677,024. Oxygenation of living tissue is disclosed in U.S. Pat. No. 5,362,622. Using oxygen and/or oxygen containing gas mixtures in the presence of a circulating nutrient is another method wherein gases and/or gas mixtures have been used for organ and tissue preservation as disclosed in U.S. Pat. No. 3,772,153.

Even with these various processes, there still exists a need for a process in which the deformation of cellular components and fragmentation of bio-molecules such as RNA, DNA and proteins are minimized or completely eliminated since such materials are not adequate for use in diagnostic and prognostic processes as well as currently available research applications. Many prior art processes prove to be less than desirable when preserving biological materials for extended periods of time due to damage to the biological materials caused by the actual preservation process utilized. Depending upon the conditions of preservation and/or storage, the biological materials may tend to degrade more rapidly than normal and to the degree that they cannot successfully be used for biological/medical research purposes. As time progresses, materials preserved in such manners are typically less and less acceptable for their intended purpose due to structural breakdown of the sample as well as the breakdown of cellular components such as DNA, RNA and proteins. Accordingly, there is a need for a process for preserving biological materials which not only slows down or eliminates the degradation of the structural integrity of biological materials but also minimizes or eliminates the degree of degradation of cellular components such as DNA, RNA and proteins.

SUMMARY OF THE INVENTION

The present invention relates to a process for extending the preservation of biological materials that comprises subjecting the biological material to a fixation process and then packaging the biological material in a container under a controlled atmosphere of noble gas in order to allow for long term storage of the biological material. The controlled atmosphere of noble gas of the present invention comprises one or more noble gases selected from argon, xenon, helium, neon, krypton and radon. Optionally, the controlled atmosphere of noble gas may include one or more additional gases selected from nitric oxide, hydrogen, hydrogen sulfide, carbon monoxide, carbon dioxide, nitrogen and oxygen.

DETAILED DESCRIPTION OF THE INVENTION

The process of the present invention involves the extended preservation of biological materials. The process is directed to the preservation of biological materials so that these materials may be stored for use at a later time for diagnosis, prognosis and further research applications in the biological and medical fields.

In the present invention, biological materials are preserved by contacting the biological materials to be preserved with a controlled atmosphere of a noble gas in a container that is capable of being sealed in a manner to prevent the escape of the controlled atmosphere of noble gas. In an alternative embodiment, ideally the container is capable of minimizing the penetration of light into the container.

As used herein the phrase "biological materials" refers to cellular samples and tissue samples obtained from either a human or an animal (of human or animal origin) which will be subjected to a process in which the materials are fixed to allow for storage for later examination.

Furthermore, as used herein, the phrase "cellular sample (s)" refers to any one or more protoplasmic masses that makes up organized tissue. Said cellular samples may be in the form of individual cells or mixtures of individual cells that originate from the same or different sources. The cellular sample (s) to be preserved may be in a dry, semi-dry or liquid state prior to preparation of the cellular samples for preservation. Non-limiting examples of such cellular sample(s) that are contemplated to be preserved according to the process of the present invention include whole blood, blood plasma, red blood cells, semen, saliva, urine, peritoneal fluid, amniotic fluid and stem cells.

As used herein, the phrase "tissue sample(s)" refers to an aggregation or group of similarly specialized cellular sample (s) organized into a functional unit and united in the performance of a particular function. These tissue samples can be from a particular organ or can be integrated with other tissues to form part of an organ. Such tissue samples may be in the form of small pieces, slices or larger samples of these organs. Non-limiting examples of tissue samples that are contemplated to be preserved according to the process of the present invention includes connective, nervous, epithelial and muscle tissue. More specifically, non-limiting examples include bone, tendons, ligaments, cartilage, fat, reproductive tissue, various glands, pancreas, gastrointestinal tract, tumors, lung, stomach, muscle, kidney, breast, brain, skin, uterine and bladder.

Note that within the context of the present invention, the biological materials utilized are cellular materials and tissue samples which will be "preserved" or "fixed" for future use. As used herein, the phrase "preserved" or "fixed" refers to biological samples which have been subjected to a substance or preparation for the purpose of limiting, slowing down, or destroying the biological reactions of the sample such as for example the enzymatic activity of the sample or the multiplication of the microorganism. In other words, the materials are subjected to a process to ensure the prevention of damage or changes in the morphological, epitopic or identifying properties of the tissues that are being processed. In the most preferred embodiment of the present invention, the biological material(s) to be subjected to the controlled atmosphere of noble gas are immunohistological/histopathological samples that have been prepped and sectioned.

As noted above, the biological material(s) to be preserved are contacted with a controlled atmosphere of noble gas. The controlled atmosphere of noble gas utilized in the present invention may comprise one noble gas or a mixture of two or more noble gases. In one optional embodiment, the controlled atmosphere comprises one or more noble gases in combination with one or more additional gases which are not noble gases. The noble gases utilized in the present process include argon, xenon, helium, neon, krypton and radon. Of these noble gases, the preferred noble gases for use include argon and xenon or mixtures of argon and xenon.

Accordingly, in one preferred embodiment of the present invention the biological material(s) to be preserved will be contacted with 100 volume percent of argon gas (a controlled atmosphere of pure argon).

In an alternative preferred embodiment of the present invention, the biological material(s) to be preserved will be contacted with 100 volume percent of xenon gas (a controlled atmosphere of pure xenon).

In a still further embodiment, the biological materials may be exposed to mixtures of noble gases. In such a case, the controlled atmosphere of noble gas may comprise a mixture of two or more noble gases selected from argon, xenon, helium, neon, krypton and radon. With regard to this particular embodiment, when two noble gases are present, the preferred ratio of the first noble gas to the second noble gas will to some degree be dependent upon the type of biological material(s) being preserved. Typically, the amount of the first noble gas in the noble gas mixture will range from about 5 volume percent to about 95 volume percent with the remaining amount in the gas mixture comprising the second noble gas. In this particular embodiment, the preferred mixture is a gas mixture comprising argon and xenon wherein the amount of argon present in the noble gas mixture ranges from about 5 volume percent to about 95 volume percent with the remaining amount in the gas mixture being xenon (from about 95 volume percent to about 5 volume percent). Preferably, when the noble gas comprises a mixture of argon and xenon, the amount of argon present in the gas mixture ranges from about 25 volume percent to about 75 volume percent with the remaining amount in the gas mixture being xenon (from about 75 volume percent to about 25 volume percent).

As noted, the controlled atmosphere of noble gas may also comprise greater than two noble gases. In such cases, as when two noble gases are present, the final ratio of the gases to one another will likely take into consideration the type of cellular material or tissue to be preserved. When three noble gases are present in the controlled atmosphere of noble gas, the ratio of the three will likely be such that the first noble gas is present in an amount from about 5 volume percent to about 95 volume percent with the remaining amount in the gas mixture being a combination of the second and third noble gases with the ratio of the second to third gas being such that the second gas is present in an amount from about 25 volume percent to about 75 volume percent of the remaining amount in the gas mixture that comprises the second and third gas mixture with the remainder of this portion being the third noble gas. Preferably, when three noble gases are present in the controlled atmosphere of noble gas, the ratio of the three will likely be such that the first noble gas is present in an amount from about 25 volume percent to about 75 volume percent with the remaining amount in the gas mixture being the second and third noble gases.

In a still further embodiment of the present invention, the controlled atmosphere of noble gas comprises one or more noble gases in combination with one or more additional gases selected from nitric oxide, hydrogen, hydrogen sulfide, carbon monoxide, carbon dioxide, nitrogen and oxygen. In this embodiment, when only one noble gas is present in the gas mixture with one or more additional gases, the noble gas will typically be present in an amount from about 50.000 volume percent to about 99.999 volume percent with the remainder of the gas mixture comprising one or more additional gases selected from nitric oxide, hydrogen, hydrogen sulfide, carbon monoxide, carbon dioxide, nitrogen and oxygen, preferably in an amount from about 75.000 volume percent to about 99.999 volume percent with the remainder of the gas mixture comprising one or more additional gases selected from nitric oxide, hydrogen, hydrogen sulfide, carbon monoxide, carbon dioxide, nitrogen and oxygen. Of the additional gases utilized in combination with one noble gas, preferably the one or more additional gases will be selected from carbon monoxide, nitric oxide and hydrogen. One preferred controlled atmosphere of noble gas under this particular embodiment comprises argon in an amount from about 50.000 volume percent to about 99.999 volume percent with the remainder of the atmosphere of noble gas comprising one or more of carbon monoxide, nitric oxide and hydrogen, with the amount of the additional gas included as remainder depending upon the actual gas used. In an alternative, the preferred controlled atmosphere of noble gas comprises xenon in an amount from about 50.000 volume percent to about 99.999 volume percent with the remainder comprising one or more of carbon monoxide, nitric oxide and hydrogen, with the amount of the additional gas included as remainder depending upon the actual gas used.

It is also contemplated to utilize two noble gases in combination with one or more additional gases selected from nitric oxide, hydrogen, hydrogen sulfide, carbon monoxide, carbon dioxide, nitrogen and oxygen. When this is the case, the noble gas mixture will typically comprise from about 50.000 volume percent to about 99.999 volume percent of the atmosphere of noble gas with the remaining volume percent being the one or more additional gases noted. The particularly preferred controlled atmosphere of noble gas in this embodiment is a mixture of argon and xenon in combination with one or more additional gases selected from nitric oxide, carbon monoxide and hydrogen. In this particularly preferred controlled atmosphere, the controlled atmosphere of noble gas comprises a mixture of argon and xenon that comprises from about 50.000 volume percent to about 99.999 volume percent of the controlled atmosphere of noble gas with the ration argon to xenon being as described hereinbefore.

Note that when the controlled atmosphere comprises mixtures of gases (i.e., two or more noble gases or one or more noble gases in combination with one or more additional gases), the gases of the controlled atmosphere may be introduced into the container in a pre-mix state or in a separate state. As used herein the phrase "pre-mix state" refers to a state in which the gases are mixed either right before they are utilized in the process or well before they are utilized in the process. As used herein, the phrase "separate state" refers to a state in which the gases are incorporated into the process separately, either all at the same time but with separate gas lines or through one line but one gas at a time (one followed by another). The pressure inside of the container can range from about atmospheric to about seven hundred atmospheres.

The container utilized in the process of the present invention can be any container that is capable of being sealed. In an alternative embodiment, the container is capable of being sealed and also capable of limiting the amount of light that enters the container. Accordingly, the container may be of any shape or size provided that it meets the above criteria and provided that it is sufficient to hold the biological material(s) to be preserved. While the size of the container is not a critical aspect to the present invention, the size should be dependent upon the size of samples normally preserved for diagnostic, prognostic or research purposes. For example, it would be possible to use pouches of the following dimensions as containers: 16 inches by 24 inches, 8 inches by 12 inches and 4 inches by 5 inches. Note that containers having differing heights, widths and depths are contemplated to be within the scope of the containers utilized with the only real determining factor being the size of the sample to be preserved. Note that while the invention is contemplated to work with larger sizes of samples, it is thought that smaller samples will be more prone to the preservation extension offered by the present invention due to the greater penetration thought to occur with regard to the controlled atmosphere of noble gas (with regard to the inner reaches of the sample being preserved).

Non-limiting examples of the types of containers that may be used include containers in the form of a shaped container having a lid, such as a rectangular or square shaped box with a lid, or a tubular shaped container with a lid, or a test tube with a lid, a package in the form of a bag, pouch or gas tight plexiglass container. The container may be glass, glass with a plastic lid, glass with a rubber lid, metallic film, plastic film. While not necessary, in some instances the container utilized can be a sterile container. However, in most instances, the container will not be a sterile container but will instead be a clean container that is relatively free of debris and contaminants.

In those embodiments where the container is such that it limits the amount of light the enters the container, each part of the container should limit light penetration into the container once the container is sealed. Accordingly, the container may be opaque to allow a small amount of light to enter or completely tinted, dyed, painted, or colored in any manner known to those of ordinary skill in the art in order to prevent the penetration of light into the container once the material or sample is processed according to the process of the present invention. In one of the more preferred embodiments of the present invention, the container comprises a metallic flexible bag or pouch that is capable of being sealed in order to retain the controlled atmosphere of noble gas once the controlled atmosphere of noble gas is introduced into the container.

The main step of the process of the present invention comprises placing the biological material(s) to be preserved in a suitable container as defined hereinbefore and then contacting the biological material(s) with a controlled atmosphere of noble gas as defined hereinbefore. This container allows for the controlled atmosphere of noble gas to be maintained for the biological material(s) for the duration of the storage of the biological material(s). The application of the controlled atmosphere to the biological material(s) may be accomplished in any manner that is known in the art. For example, the application of the controlled atmosphere of noble gas in the container containing the biological material(s) may be accomplished by flushing the container with the controlled atmosphere of noble gas for a period of time sufficient to replace the original atmosphere of the container; to replace the original atmosphere with the controlled atmosphere of noble gas. Alternatively, vacuum may be used to remove the atmosphere in the container containing the biological material(s) followed by the introduction of the controlled atmosphere of noble gas (for example, removing the air by vacuum and then introducing argon). By packaging the biological material(s) in such a fashion, it has been found that this allows for more long term storage of the biological material(s) since this is thought to minimize or possibly eliminate the degradation of biological material(s) thereby extending the time period in which such materials can be shelved before use for diagnostic, prognostic or research applications.

In the process of the present invention, before subjecting the biological material(s) to the controlled atmosphere of noble gas, multiple steps are taken to preserve the biological material(s). Accordingly, the steps of the present process comprise subjecting the biological material(s) to a fixation process followed by packaging the biological material(s) in a container under a controlled atmosphere of noble gas. While any number of fixation processes are contemplated to be within the scope of the present invention, the preferred fixation process is the formalin fixed paraffin embedded process.

In one such embodiment, the steps involve: preparing formalin fixed paraffin embedded samples and then subjecting these samples to contact with the controlled atmosphere of noble gas in a sealed container. More specifically, the steps include removing the biological material(s) to be preserved, fixing the biological material(s) with a fixative solution, dehydrating the biological material(s) using a graded alcohol, clearing and impregnating the biological material(s) with a clearing agent, and then embedding the biological material(s) in paraffin. The process further optionally includes sectioning the biological material(s) and mounting the sectioned biological material(s) on slides. The prepped biological material(s) are then subjected to packaging as described herein under controlled atmosphere as described herein for long term storage at room temperature.

With regard to the preparation of the biological material(s), the removal of the biological material(s) will to some degree depend upon the source of the biological material(s) to be preserved. More specifically, in the case of research samples, the cellular materials or tissue sample are often materials or samples which are excised from a particular source. For example, the biological material(s) may be taken from a live host as in the case of blood or tumor biopsies or taken from a host that is sacrificed as in the case of research animals in which certain tissue is excised. The requirement is that there be at least one intact cell in order to provide for a sufficient material or sample to be processed. Preferably, there are multiple intact cells. In each case, the biological material(s) may be extracted or excised using standard known and used protocols that have been established for the removal of such materials.

Once the biological material(s) has been obtained, this biological material(s) is typically placed in a receptacle and directly taken to the next step of fixation. In many instances though, it is not possible to proceed with fixation immediately. In such cases, the biological material(s) can be placed in a clean receptacle which is then stored until it is possible to process the biological material(s). In such cases, the biological material(s) are typically maintained at a temperature from about 2° C. to about 23.5° C. for a short period of time. Preferably, the biological material(s) is maintained under refrigeration until subjected to the process of the present invention. In some instances, the biological material(s) may be frozen. Accordingly, with regard to the preferred embodiment, after the biological material(s) is placed in the clean receptacle, the receptacle containing the biological material(s) is refrigerated at a temperature from about 2° C. to about 7° C. While the biological material(s) may be maintained (refrigerated or at room temperature) for a period of time (i.e., from as low as 2 hours up to 48 hours), it is thought that preservation utilizing the process of the present invention is best with regard to biological material(s) that are preferably subjected to the process of the present invention as soon possible in order to minimize the degree of normal degradation that begins to occur immediately after the sample is separated from the living host.

The next step in the process involves subjecting the biological material(s) to fixation with a fixative solution, preferably a buffered fixative solution, preferably having a pH of about 7.0. A variety of different fixative processes using solutions are known to those of ordinary skill in the art and may be utilized as a part of the present process. Such processes typically involve placing the cellular material of tissue sample in a neutral buffered formalin mixture for a specified period of time—normally from about 4 to about 72 hours, preferably from about 12 hours to about 36 hours, even more preferably from about 18 hours to about 24 hours. More specifically, the fixative solution used comprises Tris-, phosphate-, and $CaCl_2$-buffered formalins or formalin without buffer. Such fixative solutions are also commercially available from a variety of vendors. In addition, prior to being fixed in the fixative solution, the biological material(s) may be first washed in a neutral solution to remove any excess debris that may be present.

After the biological material(s) have been subjected to the fixative solution as noted above, they are then subjected to a variety of sample processing steps in order to prepare the samples for being embedded in paraffin. The general objective of these steps is to prepare the samples for the replacement of water within the samples with paraffin. More specifically, the fixed biological material(s) are subjected to a variety of steps which include dehydration using a graded alcohol series and clearing with a clearing agent to remove any of the dehydrating agent that may still be present. With regard to the first step in these processing steps, the biological material(s) is usually dehydrated by transferring the biological material(s) through a graded alcohol series, through a series of solutions of increasing alcohol concentrations. Of the know alcohols, ethanol is the preferred alcohol. One alternative is to use an alcohol mixed with formalin for at least one of the steps in the series. While other dehydrants can be used, it has been found that these other dehydrants such as acetone and dioxane demonstrate certain disadvantages. More specifically, with regard to dehydration, the biological material(s) is subjected to multiple baths or exposures of alcohol at varying increasing concentrations. For example, the biological material(s) are subjected to from 2 to 6 different ethanol stations wherein the concentration of ethanol in the first of the series is from about 70% and the last in the series is about 100%. The amount of time that the biological material(s) are subjected (immersed or exposed) to each station of alcohol will be dependent upon the actual size of the sample that is being processed. In general, such samples will be subjected to each station for a period of from 0.5 hours to 3.0 hours each.

After being subjected to alcohol multiple times, the biological material(s) are then subjected to a clearing step which allows for the removal of the dehydrant used so that the paraffin is more likely to embed in the biological material(s) being preserved. This step involves subjecting the biological material(s) to clearing agent one or more times in order to clear the alcohol contained in the biological material(s) and replace this alcohol with the clearing agent. The clearing agents that may be used include, but are not limited to xylene, toluene, chloroform and methyl salicylate. Typically the number of times the sample is cleared (brought into contact with the clearing agent) will range from 1 to 4 with the preferred number being from one to two. In such cases, the biological material(s) will be subjected to the clearing agent for a period of time ranging from about 0.5 hours to about 2 hours.

Once the biological material(s) have been processed as noted above, they are then subjected to paraffin embedding. Those of ordinary skill in the art will recognize that a variety of different paraffin embedding processes are known in the art. Such processes may be utilized in the preparation of the biological material(s) of the present invention. Typically, in order to paraffin embed a sample, the sample is subjected to paraffin a varying number of times (from 2 to 5) for varying periods of time to allow for infiltration of the sample with the paraffin. For example, the biological material(s) may be subjected 4 separate times for the same or varying amounts of time, for example for 5 minutes, 10 minutes, 20 minutes and 40 minutes, respectively or any of these times each of the four times.

This formalin fixing paraffin embedding process may be accomplished in any manner but is typically carried out utilizing any one of the commercially available automated tissue processing apparatus for preparing samples in such a manner. Such apparatus is typically able to be programmed with the actual steps needed. In addition, such apparatus allows for the conducting of the process at specific temperatures and under specific atmospheres since the application of a higher temperature and vacuum is often utilized to assist penetration of the paraffin. Such measures are readily known by those of ordinary skill in the art.

The paraffin utilized may be any type of paraffin utilize in the art for fixing materials such as those of the present invention. Once the biological material(s) are embedded, they are then sectioned into the desired size of sample. Most often, the embedded biological material(s) are sliced to a thin slice of from about 3 to about 10 microns, usually from about 4 to about 8 microns although larger (thicker) sections may be used. As the sections are cut they float on a warm water bath. They are then picked up and placed on a glass microscope slide. Typically the glass slides can be heated in a warm oven for a short period of time (from about 5 minutes to 20 minutes) in order to facilitate the sections adhering to the slides. The sample is then typically covered with a glass coverslip for further protection of the sample. Once again, processes and apparatus for sectioning are known in the art and are readily available for making such sections. Technology is available to allow for sectioning of samples down to 0.1 micron. Typically the samples are prepared using a microtome. Once the various sections are prepared, each of the sections is placed on a glass slide for storage until used for immunohistological/histopathological research, diagnosis or prognosis reasons.

Once the above steps are carried out, the processed samples of biological material(s) are then placed in the container for final packaging where they are then subjected to packaging under the controlled atmosphere as defined hereinabove to allow for long term storage at room temperature. As indicated above, this is accomplished by removing the atmosphere in the container in some manner followed by replacing this atmosphere with the controlled atmosphere of noble gas.

As noted above, the present process is geared toward the preparation of preserved biological materials, more noteably immunohistological/histopathology samples for use in the diagnosis/prognosis of disease and research. It should also be recognized that with the ever increasing use of forensic technology in solving crimes, there is also a vast need for a process to allow for extended preservation of samples obtained from a crime scene. Accordingly, the above noted process would also be useful in the in the preservation of samples for forensic purposes.

EXAMPLES

Tissue samples were prepared by fixation and subjected to a controlled atmosphere of noble gas to determine if degradation of the DNA, RNA or proteins of the samples could be minimized or eliminated. The general procedure followed included fixing the samples in a formalin buffer followed by embedding them in paraffin. Once the tissue was fixed, it was then sectioned to make thin microscopic sections for immunohistological/histological purposes.

Mouse kidneys were fixed in formalin then processed using dehydration and clearing steps thereby allowing the mouse kidneys to be infiltrated with paraffin. The water from each tissue sample was removed by subjecting the tissue sample to dehydration using a series of different grades of ethanol. The tissue samples were subjected to dehydration were then subjected to clearing which consisted of the removal of the ethanol with xylene (an agent that that will be miscible with the embedding medium (paraffin)). In the next step, the tissue sample was embedded with paraffin. Slides prepared in the above manner were then individually packaged in metallic pouches utilizing the variety of gas mixtures as noted below. Multiple slides were prepared for each control and for each sample. More specifically, separate sample dates were set (dates for examination of prepared slides) with sets of slides for each condition/control prepared to correspond to each sample date. Accordingly, sufficient slides were prepared for each gas condition/control to allow analysis of a slide on each date for each gas condition/control. Each of the tissue samples was then subjected to the controlled atmosphere noted below:

Control 1—NP-air
Control 2—V-vacuum-packaged
Sample 1—100% argon (G1)
Sample 2—100% xenon (G2)
Sample 3—1% H2S with a balance of N2 (G3)
Sample 4—1% CO with a balance of N2 (G4)

More specifically, the slides were placed in metallic pouches, subjected to a vacuum flush and then the head space gas-sealed (four volumes of gas/1 volume of tissue/slide) using a flow meter to calculate the gas volume based upon gas specific gravity for each individual gas. A pouch sealer was then used to seal each pouch. After being packaged, the slides are stored under ambient conditions until analyzed. At varying times (with the anticipated analysis being generally 0, 2 weeks, 4 weeks, 8 weeks and 17 weeks), the tissue samples are analyzed to determine whether degradation of the DNA, RNA or protein of the tissue were slowed down or altogether eliminated (to determine the protein and nucleic acid stability and integrity).

At the times noted, standard assays were performed to determine the stability of proteins or RNA. With regard to the protein assay, proteins were extracted from the samples and subjected to the standard assay. In the case where the proteins were broken down, the assay did not work well. The final conclusion after 8 weeks with regard to the results obtained from the protein assay was that samples 1 and 2 were as good as samples 3 and 4 in preserving the proteins.

With regard to the RNA assay, after 8 weeks samples 1 and 2 gave promising results (the best overall RNA integrity) with no difference noted in terms of processing times. Sample 1 gave the best overall results. Of the remaining samples, sample 4 gave intermediate results and sample 3 gave the least promising results of the four gases tested.

What is claimed:

1. A process for preserving a biological material that contains RNA molecules, said process comprising subjecting the biological material to a fixation process and then packaging the biological material in a container having a controlled atmosphere of noble gas, wherein the controlled atmosphere of noble gas is selected from the group consisting of argon, xenon, and combinations thereof, wherein the rate of degradation of the RNA molecules in the biological material having the controlled atmosphere of noble gas relative to a controlled atmosphere consisting essentially of nitrogen gas is reduced.

2. The process of claim 1, wherein the controlled atmosphere of noble gas consists of pure argon or pure xenon.

3. The process of claim 2 wherein the controlled atmosphere of noble gas is pure argon.

4. The process of claim 2, wherein the controlled atmosphere of noble gas is pure xenon.

5. The process of claim 1, wherein the amount of argon present in the controlled atmosphere is an amount from about 50 volume percent to about 99.999 volume percent argon.

6. The process of claim 5, wherein the amount of argon present in the controlled atmosphere is an amount from about 90 volume percent to about 99.999 volume percent argon.

7. The process of claim 1, wherein the amount of xenon present in the controlled atmosphere is an amount from about 50 volume percent to about 99.999 volume percent xenon.

8. The process of claim 7, wherein the amount of xenon present in the controlled atmosphere is from about 90 volume percent to about 99.999 volume percent xenon.

9. The process of claim 5, wherein the amount of argon present in the controlled atmosphere is an amount from about 50 volume percent to about 95 volume percent argon.

10. The process of claim 5, wherein the amount of xenon present in the controlled atmosphere is an amount from about 50 volume percent to about 95 volume percent xenon.

11. The process of claim 1, wherein the fixation process comprises:
    a) fixing the biological material with a formalin solution;
    b) embedding the biological material in paraffin;
    c) sectioning the paraffin embedded biological material in order to obtain biological material sections; and
    d) placing the sections obtained in step (c) on slides.

12. The process of claim 1, wherein the fixation process comprises:
    a) fixing the biological material with a buffered fixative solution;
    b) dehydrating the biological material using a graded alcohol;
    c) clearing and impregnating the biological material with a clearing agent;
    d) embedding the biological material in paraffin;
    e) sectioning the paraffin embedded biological material in order to obtain biological material sections; and
    f) mounting the sections obtained in step (e) on slides.

13. A process for preserving biological material, said process comprising the steps of:
    a) obtaining a biological material sample having at least one intact cell;
    b) fixing the biological material with a buffered fixative solution;
    c) embedding the biological material in paraffin;
    d) sectioning the paraffin embedded biological material in order to obtain biological material sections;
    e) mounting the sections obtained in step (d) on slides;
    f) providing a container that is capable of being sealed to prevent the escape of any controlled atmosphere introduced into the container;
    g) introducing the sections into the container; and
    h) contacting the sections in the container with a controlled atmosphere of a noble gas, wherein the controlled atmosphere of noble gas is selected from the group consisting of argon, xenon, and mixtures thereof,
    wherein the sectioned biological material contains RNA molecules and wherein in the controlled atmosphere the rate of degradation of the RNA molecules in the sectioned biological material having the controlled atmosphere of noble gas relative to a controlled atmosphere consisting essentially of nitrogen gas is reduced, thereby preserving the biological material.

14. The process of claim 13, wherein prior to step (c), the process further comprises the steps of dehydrating the biological material using a graded alcohol and clearing and impregnating the biological material with a clearing agent.

15. The process of claim 14, wherein the biological material is dehydrated by transferring the biological material to be preserved through a series of ethanol solutions that are increasing in concentration with each successive solution in the series.

16. The process of claim 14, wherein both prior to step (c) and after step (e), the process further comprises the steps of dehydrating the biological material using a graded ethanol and clearing or impregnating the biological material with xylene.

17. The process of claim 13, wherein the container is adapted to minimize light penetration into the container.

* * * * *